United States Patent [19]
Noble et al.

[11] Patent Number: 5,721,207
[45] Date of Patent: Feb. 24, 1998

[54] METHOD FOR TREATMENT OF PAIN

[75] Inventors: John Fowler Noble, Pomona, N.Y.; Henry Baxter Abajian, Hillsdale, N.J.

[73] Assignee: Innapharma, Inc., Upper Saddle River, N.J.

[21] Appl. No.: 424,866

[22] Filed: Apr. 18, 1995

[51] Int. Cl.$^6$ ............................................. A61K 38/00
[52] U.S. Cl. .................... 514/9; 514/11; 514/8
[58] Field of Search ............................ 514/9, 11

[56] References Cited

U.S. PATENT DOCUMENTS

| | | | |
|---|---|---|---|
| 4,086,221 | 4/1978 | Sakakibara et al. | 260/112.5 |
| 4,758,550 | 7/1988 | Cardineaux et al. | 514/12 |
| 4,977,139 | 12/1990 | Yamada et al. | 514/11 |

OTHER PUBLICATIONS

Fraioli et al. Evr. J. Pharmacology, vol. 78 pp. 381–382 (1982).
Hirota et al., Gan to Kagan Ryoho (1990), 17(5), 1059–63 (Abstract).
Braga, P.C. et al., (1993) *Neurosci. Lett. (Netherlands)* 151, (1):85–88 (abstract only).
Pasqualucci, C. et al. (1992) *Biol. Mass. Spectrum* 21:144.
Jaeger, H. and Maier, C. (1992) *Pain* 48:21–27.
Sasaki, F. et al. (1991) *Japan J. Cancer Chemother.* 18,3:437 (English translation).
Hirota, Y. et al. (1990) *Japan J. Cancer Chemother.* 17,5:1059 (English translation).
Blanchard, J. et al. (1990) *J. of Pain and Symp. Manag.* 5,1:42–45.
Miseria, S. et al. (1989) *W.J.S.* 75,2:183–184 (abstract only).
Lutze, M. et al. (1988) *Intensivemedizin* 25:196.
Tokunaka, S. et al. (1988) *Acta Urol. Jpn.* 34:1273–1277 (English translation).
Gennari, C. and Agnusdei, D. (1988) *Current Therapeutic Research* 44,5:712–721.
Shiraldi, G.F. et al. (1987) *Int. J. Clin. Pharmacol. Ther. Toxicol. (Germany)* 25, 4:229–232.
Serdengecti, S. et al. (1986) *Int. J. Clin. Pharmacol. Res.* 6,2:151–155 (abstract only).
Fiore, C.E. et al. (1985) in *Calcitonin*, A. Pecile (ed.), Elsevier Science Publishers B.V.
Fraioli, F. et al. (1982) *Europ. J. Pharmacol.* 78:381–382.
Morikawa, T. et al. (1976) *Experientia.* 32,9:1104–1106.

*Primary Examiner*—Cecilia J. Tsang
*Assistant Examiner*—Pihynn Tozeam
*Attorney, Agent, or Firm*—Greenlee, Winner and Sullivan, P.C.

[57] ABSTRACT

An improved method for the treatment of intractable pain is provided by the present invention. The improved method is the intrathecal administration of a therapeutic composition comprising elcatonin and a pharmaceutically acceptable carrier. Intrathecally administered elcatonin produces more potent and prolonged analgesia than elcatonin/calcitonins administered by other routes (e.g., intravenous, intramuscular injection) and/or opiates administered by different routes (including epidural or intrathecal administration).

13 Claims, 10 Drawing Sheets

METHOD FOR TREATMENT OF PAIN

FIELD OF THE INVENTION

The field of the invention is the area of the treatment of pain in humans, particularly intractable pain. Specifically, the present invention provides for the usage of elcatonin administered via an epidural or intrathecal route.

BACKGROUND OF THE INVENTION

Calcitonin has been shown to be effective for the treatment of pain in humans where pain is the result of conditions including, but not limited to, osteoporosis, Paget's disease, phantom limb pain, reflex sympathetic dystrophy, bone fractures, ankylosing spondylitis and bone metastases of malignancy [see, e.g., Gennari and Agnusdei (1988) Current Therapeutic Research 44: 712–721]. Calcitonin has been used in therapeutic compositions for its hypocalcemic and hypophosphatemic effects. Calcitonin has also been used to increase bone mass.

Narcotics such as morphine have also been used for the treatment of chronic pain in humans, have the disadvantages of addiction and the development of tolerance to nontoxic doses of morphine.

There is a long felt need in the art for a pain treatment in those patients who cannot rely on conventional analgesic treatments. Such a pain treatment should advantageously not have significant negative side effects or toxicity; further, there is a need for a pain treatment which is not associated with the development of tolerance. The present invention provides an effective treatment for pain, particularly for patients suffering from chronic and intractable pain, for example, those patients suffering from intractable pain associated with terminal cancer.

SUMMARY OF THE INVENTION

The present method provides an improved treatment for the treatment of pain in mammals, particularly the treatment of intractable pain in humans. In the present invention, elcatonin is provided by intrathecal administration to a human suffering from pain. The elcatonin is dissolved in a vehicle suitable for intrathecal injection, for example, sterile physiological saline. The dosage range is from about 0.2 to about 15 IU elcatonin per kg body weight, preferably from about 1.6 to about 6.4 IU elcatonin per kg body weight. Preferably, the composition further contains human serum albumin at a concentration from about 0.03 to 0.1% (weight/volume). The dose to be administered is preferably formulated in a standard volume for intrathecal or epidural administration, (preferably about 0.5 to about 2.0 mL for a single intrathecal injection). Elcatonin is administered via the intrathecal route, in the dosage disclosed herein, in single or multiple doses. For multiple doses, administration can be at intervals up to 24 to 48 hrs. Administration can be via bolus injections or using a continuous or pulsed delivery pump for the intrathecal or epidural routes.

The intrathecal administration of elcatonin provides a strong and prolonged analgesic effect which is not associated with significant undesirable side effects, such as addiction, and there is no significant development of tolerance. The pain treatment of the present invention is particularly helpful in patients suffering from intractable and severe pain, such as that of terminal cancer patients.

DETAILED DESCRIPTION OF THE INVENTION

Figure 1:
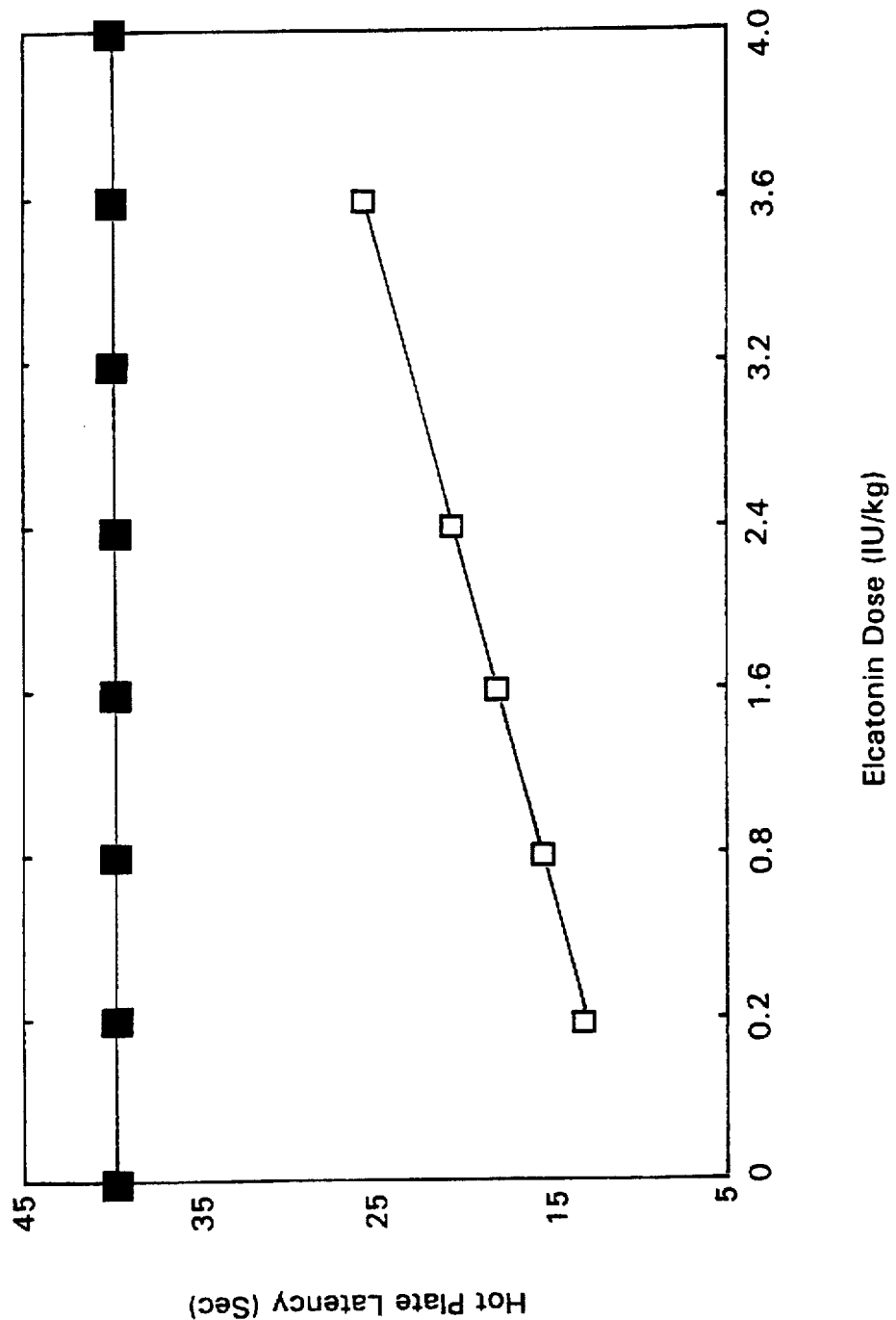
FIG. 1 illustrates that elcatonin administered via intrathecal route increases hot plate latencies in a dose related fashion. Hot plate latencies (sec) were measured 1 hr after elcatonin administration.

Elcatonin, disclosed in U.S. Pat. No. 4,086,221 (Shumpei Sakakibara et al., filed May 3, 1976), has the following structure:

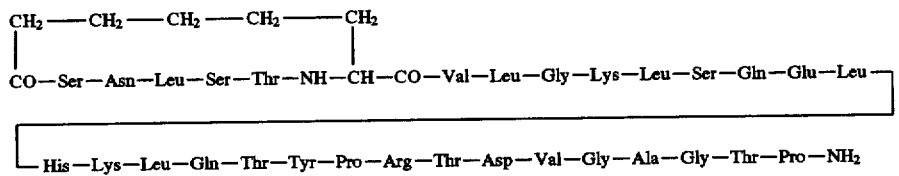

Elcatonin differs from eel calcitonin in that the cysteine residues at the N-terminal and the seventh amino acid positions are replaced with an aminosuberic acid bridge, which provides a carbon-carbon bridge in place of the disulfide bond between the cysteine residues in the natural calcitonin molecule. Other aminosuberic acid-bridged molecules are described in U.S. Pat. No. 4,086,221, incorporated by reference herein. The amino acid sequences for eel, human, porcine, salmon and rat calcitonins are given in SEQ ID Nos: 1, 2, 3, 4 and 5, respectively. Preferably, the C-terminal amino acid is in the amide form. Replacement of the N-terminal and seventh position cysteines with an aminosuberic acid bridge in the calcitonins of SEQ ID Nos: 2–5 also yields relatively stable, analgesically effective peptide compositions. U.S. Pat. No. 4,977,139 (Yamada, et al. filed Oct. 25, 1989), incorporated by reference herein, describes aqueous elcatonin compositions with improved stability to light, heat and shaking.

U.S. Pat. Nos. 4,977,139 (Yamada et al, filed Oct. 25, 1989), 5,118,667 (Adams et al., filed May 3, 1991) and 4,758,550 (Cardineaux et al., filed Dec. 3, 1986) appear to disclose the use of calcitonin and elcatonin compositions in the treatment of various types of bone and/or pain disorders, but none appears to disclose the intrathecal administration of elcatonin in the treatment of intractable pain.

Mieria et al. (1989) Tumori (Italy) 75:183–184 appeared to disclose the epidural administration of salmon calcitonin for treatment of intractable pain, but the data did not appear to support its use as an analgesic.

As used herein, an analgesic effect means that the result is an insensibility to, or a decrease in the perception of pain or of a painful or injurious stimulus without loss of consciousness. Analgesic and antinociceptive are used synonymously in the present application.

As used herein, intractable pain is that pain which does not respond to conventional analgesics, and/or that pain which persists upon development of tolerance to a narcotic analgesic such as morphine. Intractable pain can be associated with medical conditions, including, but not limited to, cancer, bone fractures, osteoporosis, post-amputation pain and certain other medical conditions.

The rat is a preferred animal model for testing compounds administered by the intrathecal route, and the rat analgesiometric hot plate test is an accepted model system for the effective treatment of pain.

As disclosed herein (see Example 8, 9; Tables 1, 2) all doses of elcatonin used produced potent and prolonged antinociception, showing an onset within 15 min post-injection, reaching a peak at 30–60 min, and lasting at least 6 hours post-injection in the rat/hot plate analgasiometric model system. Since the doses of elcatonin used often produced maximum analgesia obtainable using the hot plate test, there were no apparent differences in hot plate latencies obtained following elcatonin ranging from 0.8–3.6 IU/kg. A slightly lower response was obtained at the lowest dose (0.2 IU/kg) used. Nevertheless, even intermediate and minimal antinociceptive responses could be obtained with lower doses of elcatonin in a dose-related manner.

TABLE 1

ANALGESIC ACTIVITY (HOT PLATE LATENCY) OF ELCATONIN FOLLOWING SINGLE INTRATHECAL ADMINISTRATION IN THE RAT (Mean ± SEM)

| Dose IU/kg | No. of Rats | Hot Plate Latency (sec) Time After Administration (hr) | | | | | | |
|---|---|---|---|---|---|---|---|---|
| | | 0 | 0.25 | 0.5 | 1 | 3 | 6 | 24 |
| 0 | 21 | 11.2 ± 0.5 | 11.7 ± 0.9 | 11.5 ± 0.6 | 12.2 ± 0.8 | 11.8 ± 1.1 | 11.1 ± 0.7 | 11.5 ± 0.5 |
| 0.2 | 11 | 10.6 ± 0.8 | 13.0 ± 1.1 | 12.9 ± 0.7 | 12.7 ± 0.9 | 13.1 ± 0.7 | 12.1 ± 0.5 | 10.8 ± 0.7 |
| 0.8 | 13 | 9.8 ± 0.8 | 15.1 ± 1.5** | 15.0 ± 1.5** | 15.2 ± 1.3** | 20.0 ± 2.8** | 12.3 ± 1.0 | 11.7 ± 1.0 |
| 1.6 | 13 | 9.2 ± 0.5 | 16.4 ± 1.2** | 16.0 ± 1.0** | 16.4 ± 1.1** | 15.1 ± 0.9** | 13.6 ± 0.8** | 10.9 ± 0.4* |
| 2.4 | 13 | 9.0 ± 0.7 | 20.0 ± 1.5** | 20.1 ± 1.9** | 19.5 ± 1.8** | 21.8 ± 2.1** | 12.6 ± 1.2* | 10.3 ± 1.2 |
| 3.6 | 12 | 10.4 ± 0.9 | 19.4 ± 1.6** | 21.4 ± 1.8** | 23.5 ± 2.5** | 19.5 ± 1.0** | 15.7 ± 1.3** | 10.2 ± 1.0 |

*p ≤ 0.05 student's t-test
** p ≤ 0.05 student's t-test

In the rat hot plate analgesiometric assay data described herein, the intrathecal administration of elcatonin gave unexpectedly improved antinociceptive results as compared with intravenous injection of elcatonin (see Example 7 herein). As shown in Example 9 and FIGS. 6–8, intrathecal elcatonin also provided dramatically improved analgesia in the rat hot plate assay as compared to intrathecal morphine. Furthermore, in a comparison of the analgesic activity of morphine and elcatonin administered intrathecally, elcatonin appeared to have significantly greater analgesic activity in the rat hot plate test, and the analgesic effect of the elcatonin also appeared to be of greater duration than that of morphine (see Example 9 and FIGS. 3–6 herein).

The following examples are provided for illustrative purposes, and they are not intended to limit the scope of the invention as disclosed and claimed herein. All studies were carried out in accordance with FDA GLP regulations (21 C.F.R. 58). Any routine procedural modifications and deviations from the disclosed practice of the invention disclosed herein which are obvious to the skilled artisan are within the scope of the instant invention.

EXAMPLES

Example 1: Experimental Animals

The rat is one of the preferred species for testing compounds for analgesic activity by various US and International Regulatory Agencies. Historical information concerning Spraque-Dawley rats is available in the published literature. Adult male Spraque-Dawley rats were obtained from Sasco Inc. (Oregon, Wis.), and were allowed a 7 day acclimation period prior to use in experimentation. Rats were weighed 1 day after receipt and again after 7 days or before assignment to an experiment. Rats were assigned to experiments and treatments randomly. Any animal whose body weight differed significantly from the mean body weight of group, which showed abnormal changes in weight or which showed signs of a physical disorder was not used. Test rats were in the range of 320–420 g.

Example 2: Animal Husbandry

Animal husbandry was in accordance with the Guide for the Care and Use of Laboratory Animal Resources, National Research Council, DHHS, Publication No. NIH 85-23, 1986, and the U.S. Department of Agriculture guidelines and Animal Welfare Act. Rats were housed in environmentally controlled rooms maintained at a temperature of 18° to 26° C., generally from 18°–20° C., a relative humidity of 40 to 70% and with greater than ten room air exchanges per hour. A 12 hr light/dark cycle per day was maintained. The animals were provided access to tap water and to food (Agway Rat Chow, Agway), both ad libitum. The inventors were not aware of any contaminants in either food or water supply which could have adversely affected the experiments.

Waste material was removed from cages twice a week, or more often if necessary. Cages and feeders were sanitized every two weeks unless required more often.

Once catheterized, rats were housed individually in stainless steel cages to avoid catheter damage or destruction by cagemates. Each rat was identified by a uniquely assigned number on its cage.

Example 3: Preparation of Stock Solutions

Elcatonin ([Des-Cys$^1$,ASU$^7$]-Calcitonin, Eel; carbacalcitonin) was obtained from Bachem, Inc. (Torrance, Calif.). It was stored at −20° C., protected from light. Stock solutions of elcatonin (1 mg/mL in sterile isotonic saline, USP grade) for use in tests of analgesic activity after intrathecal injection were made fresh daily and kept on ice. Appropriate dilutions were made just prior to injection.

Sterile isotonic saline solution (0.9% w/v NaCl, USP grade) was obtained from Sigma Chemical Co. (St. Louis, Mo.).

Human serum albumin was obtained from Sigma Chemical Co. (St. Louis, Mo.). Stock solutions were 25% (wt/vol).

Morphine sulfate was obtained from Mallinckrodt, Inc. (St. Louis, Mo.). Stock solutions of morphine for intrathecal injection were prepared daily (10 mg/mL in sterile isotonic saline) and held on ice. Appropriate dilutions were made just prior to injection.

Example 4: Neurosurgical Catheterization for Intrathecal Administration of Pharmaceuticals Intrathecal catheters were surgically implanted in the rats after application of anesthetic (Nembutal, 30 mg/kg, intraperitoneal) 5–7 days prior to the test procedure. The 5–7 day period prior to testing allowed for full recovery from the surgical procedures. Each catheter (polyethylene tubing, PE 10) was inserted via a slit in the atlanto-occipital membrane, and the catheter was threaded through the sub-arachnoid space 7.5 cm so that the tip was positioned at the rostral margin of the lumbar enlargement. Each catheter was anchored to the skull with cyanoacrylate adhesive, and the skull was closed with wound clips. The free end of each catheter was heat annealed; when compositions were to be injected via the intrathecal route each composition was introduced therein using a Hamilton needle inserted into the sealed catheter.

Example 5: Assessment of Analgesic Activity

Pain sensitivity was assessed using a standard analgesiometric hot plate test (Woolfe and MacDonald (1944) J. Pharmacol. Exp. Ther. 80:300). The hot plate response was determined by placing a rat on a 55° C. copper hot plate enclosed in a plexiglass cylinder. The interval between placement on the hot plate and the response of either licking the hind paws or jumping off the hot plate was defined as the "hot plate latency." If an animal did not respond to the hot plate by licking the hind paws or by jumping off the hot plate, it was removed after 40 sec to prevent tissue damage to the paws, and the hot plate latency value assigned was 40.

Because of the technical demands of these experiments, no more than 8–9 rats were tested on a given day. Sufficient animals were studied to obtain 10–11 evaluable rats per test condition. On the study day, animals were tested for baseline hot plate responses, and then received bolus injections of test analgesic or physiological saline (control). Hot plate responses were assessed again at 15 min, 30 min, 1 hr, 3 hr, 6 hr and 24 hr after intrathecal injection of test compound or vehicle control.

Example 6: Doses Administered

All doses of elcatonin were administered as bolus injections. The following intrathecal doses of elcatonin have been tested in the single administration studies: 0.2, 0.8, 1.6, 2.4, 3.6, 4.4, 5.2 and 6.0 IU/kg or 0.03, 0.13, 0.25, 0.39, 0.58, 0.71, 0.84 and 0.97 µg/kg. The intravenous doses of elcatonin tested were 10.0, 30.0, 100.0 and 300.0 IU/kg or 1.61, 4.83, 16.1 and 48.3 µg/kg. One microgram of elcatonin corresponds to about 6.2 IU.

Example 7: Volumes Administered

All intrathecal doses were administered in volumes of 37.5 µL/kg, followed by a catheter flush of 10 µL/kg of physiological saline (single administration studies) or in volumes of 10 µL followed by a catheter flush of 8 µL of physiological saline (multiple administration studies). All intravenous doses of elcatonin were administered in a volume 0.5 mL/kg.

Example 8: Dose Response for Intrathecal Elcatonin in the Rat Analgesiometric Assay In this study, a range of doses of elcatonin administered by the intrathecal route was tested in the analgesiometric assay to establish the minimum and peak effective doses inducing analgesia and to determine dose responsiveness. The doses tested were 0.2, 0.8, 1.6, 2.4, and 3.6 IU/kg. The desired dose was injected in a volume of 37.5 µL/kg, followed by a catheter wash-out with 10 µL saline, via the intrathecal route. Baseline (pre-drug) and responses at 15 min, 30 min, 1 hr, 3 hr, 6 hr and 24 hr after the drug or vehicle injection were determined. Eleven to thirteen animals were used for each dose of elcatonin; 21 control vehicle (saline) animals were used in this study.

A total of 113 adult male rats, of weights of 350 g to 400 g, were used. Intrathecal catheters were surgically implanted as described in Example 4. Three rats died after the surgical implantation of the catheters but prior to the administration of the test composition. A fourth rat died 24 hr after the intrathecal administration of 0.8 IU/kg elcatonin.

This study demonstrated that elcatonin administered by the intrathecal route increased hot plate latencies in a dose-related fashion (See Table 1, FIG. 1). The onset of antinociception was within 15 min after injection, and a statistically significant increase in the latency period occurred between 0.25 to 3 hrs. Significant antinociception was also apparent at 6 hrs after injection at the three higher doses. In most tests, the animals returned to baseline by 24 hr post-injection (See Table 1, FIG. 2).

Data were analyzed for statistical significance, and a point estimate (mean and standard deviation) are used to analyze analgesic activity for each dose of the drug for a selected time period. Nonparametric statistics were calculated to address the level of significance of any difference between control and test group.

Figure 2:
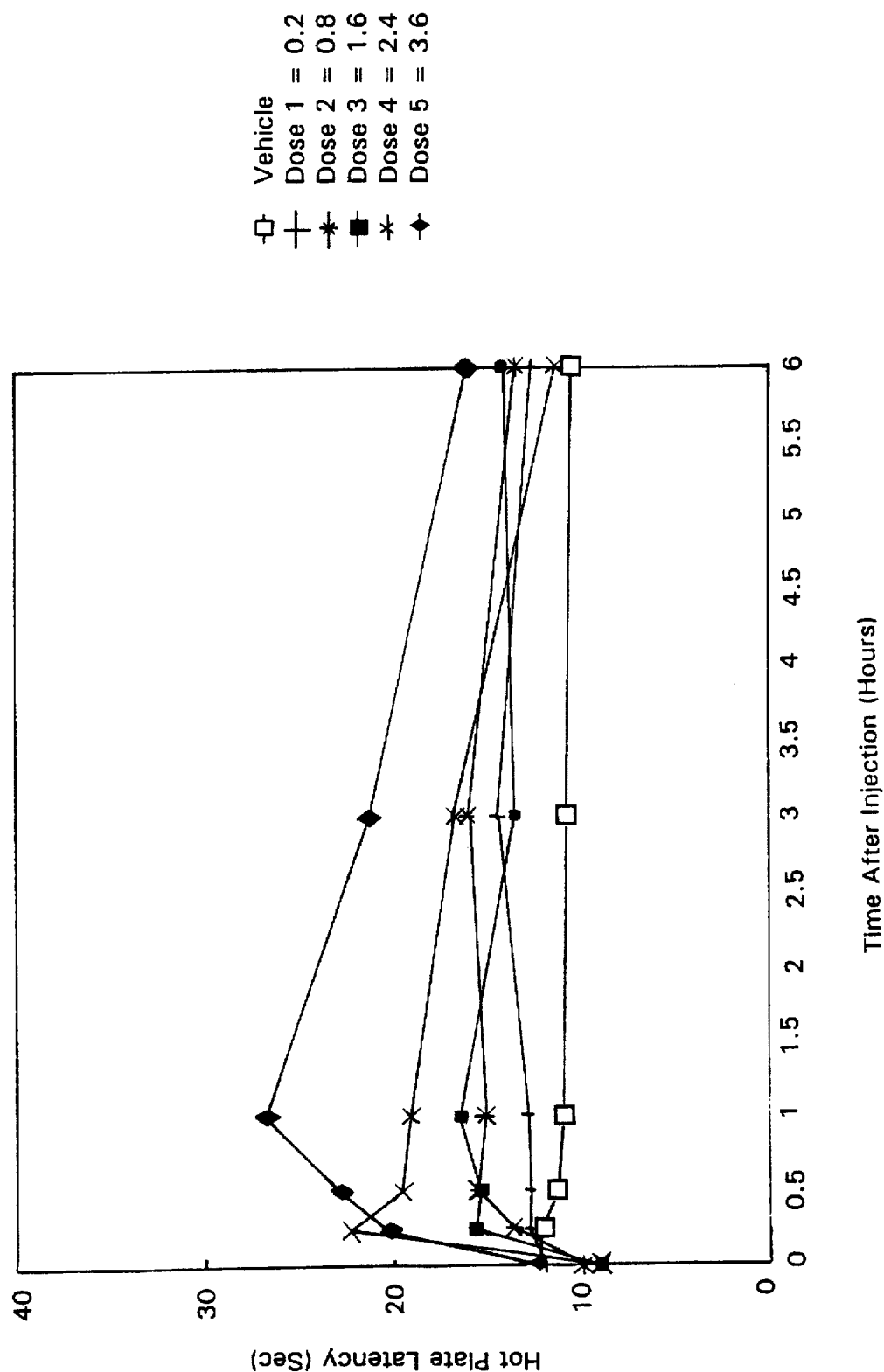
FIG. 2 illustrates the increase in rat hot plate latency after intrathecal administration of elcatonin at doses from 0.2 to 3.6 IU/kg body weight (—+—0.2 IU/kg, —*—0.8 IU/kg, —■—1.6 IU/kg, —x—2.4 IU/kg, —♦—3.6 IU/kg, —□— physiological saline control).

The lowest dose tested (0.2 IU/kg elcatonin) did not produce a statistically significant response, but doses of 0.8 and 1.6 IU/kg resulted in significant antinociception while doses of 2.4 and 3.6 IU/kg resulted in strong antinociception (FIG. 2). The administration of saline alone did not alter the baseline response in the control population.

Example 9: Analgesic Activity of Intrathecal Elcatonin vs. Intrathecal Morphine

This study compared the analgesic activities of morphine and elcatonin, each administered by the intrathecal route in the rat animal model.

Ninety-six (96) rats, ranging in weight from 320 g to 420 g, were used in this study. Catheters were implanted and recovery was allowed for as described hereinabove. Elcatonin doses were 2.4, 3.6, 4.4, 5.2, and 6.0 IU/kg (0.39, 0.58, 0.71, 0.84 and 0.97 µg/kg, respectively). Morphine sulfate was administered in doses of 37.5, 75.0 and 125.0 µg/kg. Drug or saline vehicle doses were administered using Hamilton needles inserted into the catheters, with a dose volumes of 37.5 µL/kg followed by a 10 µL saline catheter wash-out. Baseline (pre-drug) and responses at 15 min, 30 min, 1 hr, 3 hr, 6 hr and 24 hr after drug or vehicle injection were determined.

Both elcatonin (FIG. 3A) and morphine (FIG. 3B) increased hot plate latencies, indicating analgesic effects (Table 2). All tested doses of elcatonin produced potent and prolonged antinociception, showing an onset within 15 min post-injection, reaching a peak at 30–60 min, and lasting at least 6 hours post-injection (Table 2, FIG. 3A). Since the doses of elcatonin used often produced the maximum analgesia detectable using the hot plate test, there were no apparent differences in hot plate latencies obtained following elcatonin ranging from 3.6–6.0 IU/kg. A slightly smaller response was obtained when the lowest dose of elcatonin (2.4 IU/kg or 0.39 µg/kg) was used. Nevertheless, the results of Example 8 indicate that intermediate and minimal antinociceptive responses could be obtained with lower doses of elcatonin in a dose-related manner.

Figure 3A:
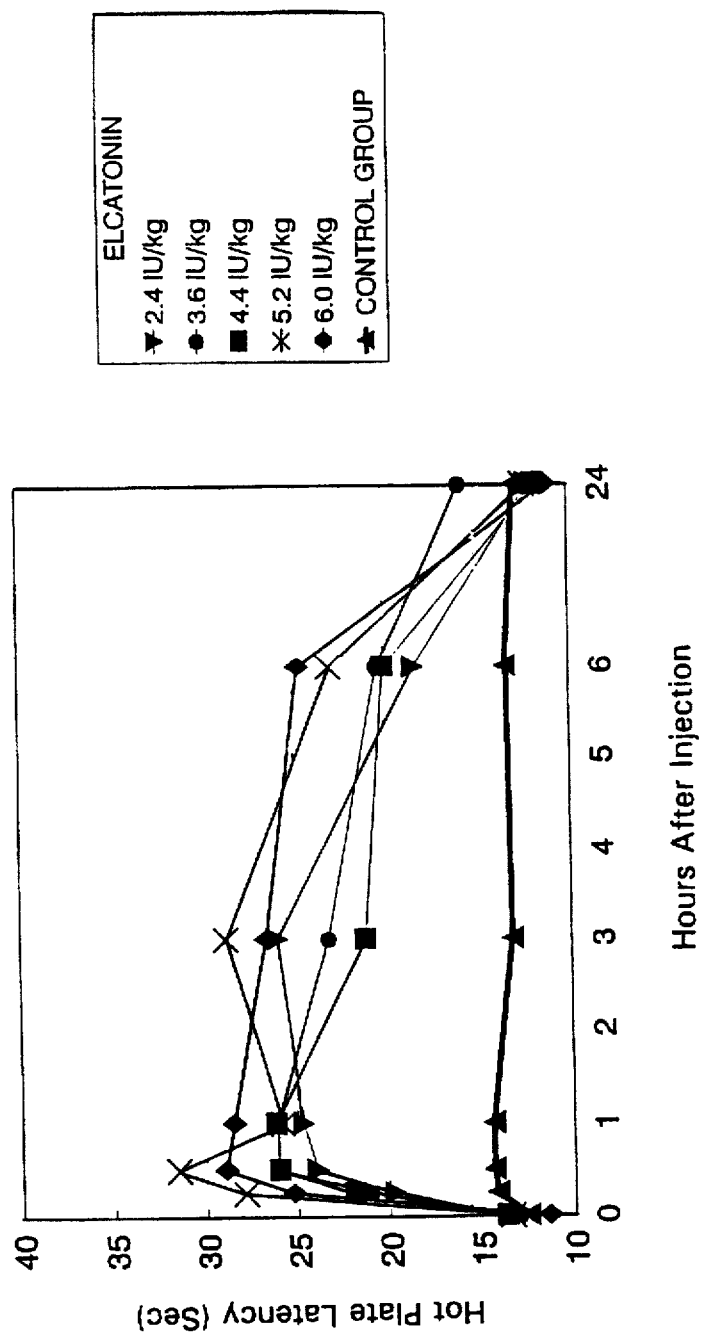
FIGS. 3A–3B provide a comparison of the increase in rat hot plate latency after intrathecal administration of elcatonin at doses from 2.4 to 6.0 IU/kg (FIG. 3A) and morphine at doses from 37.5 to 125.0 mg/kg (FIG. 3B). The maximum latency is 40 sec in these studies.
Figure 3B:
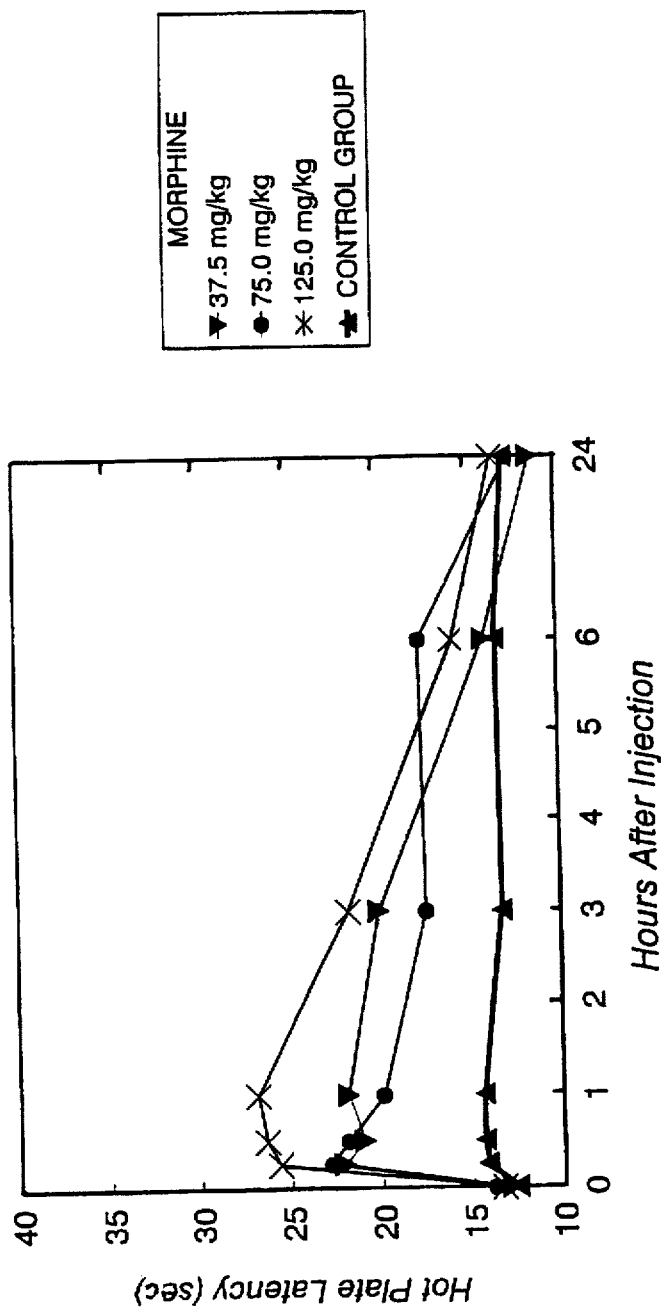
Figure 4:
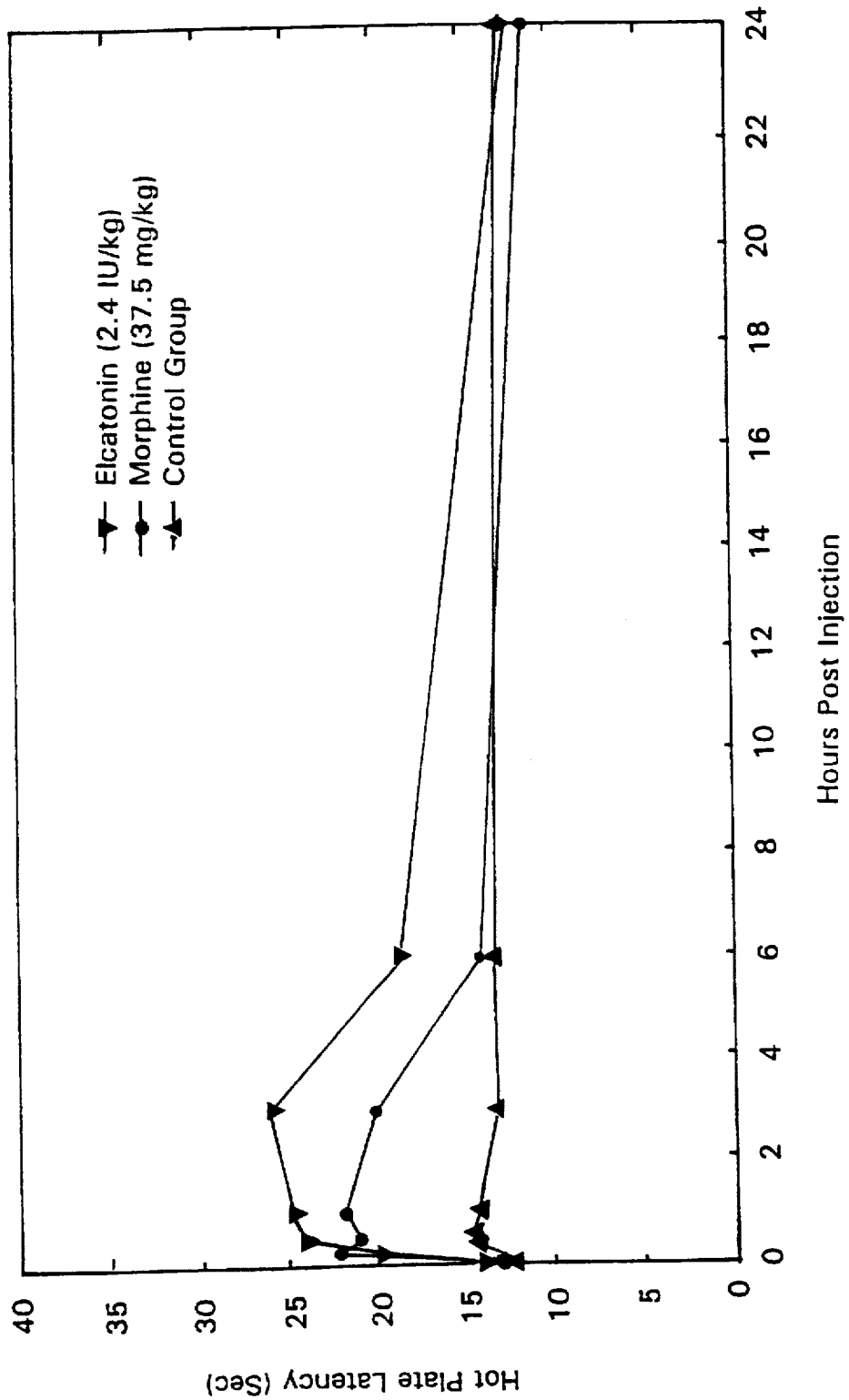
FIG. 4 provides a comparison of the time courses for increased hot plate latencies of low-dose for elcatonin (2.4 IU/kg, —●—) and morphine (37.5 mg/kg —▼—). No significant change in latency over time is observed in animals treated with physiological saline as a control. Physiological saline (—▲—) administered via the intrathecal route serves as a control. Maximum possible latent period is 40 sec.
Figure 5:
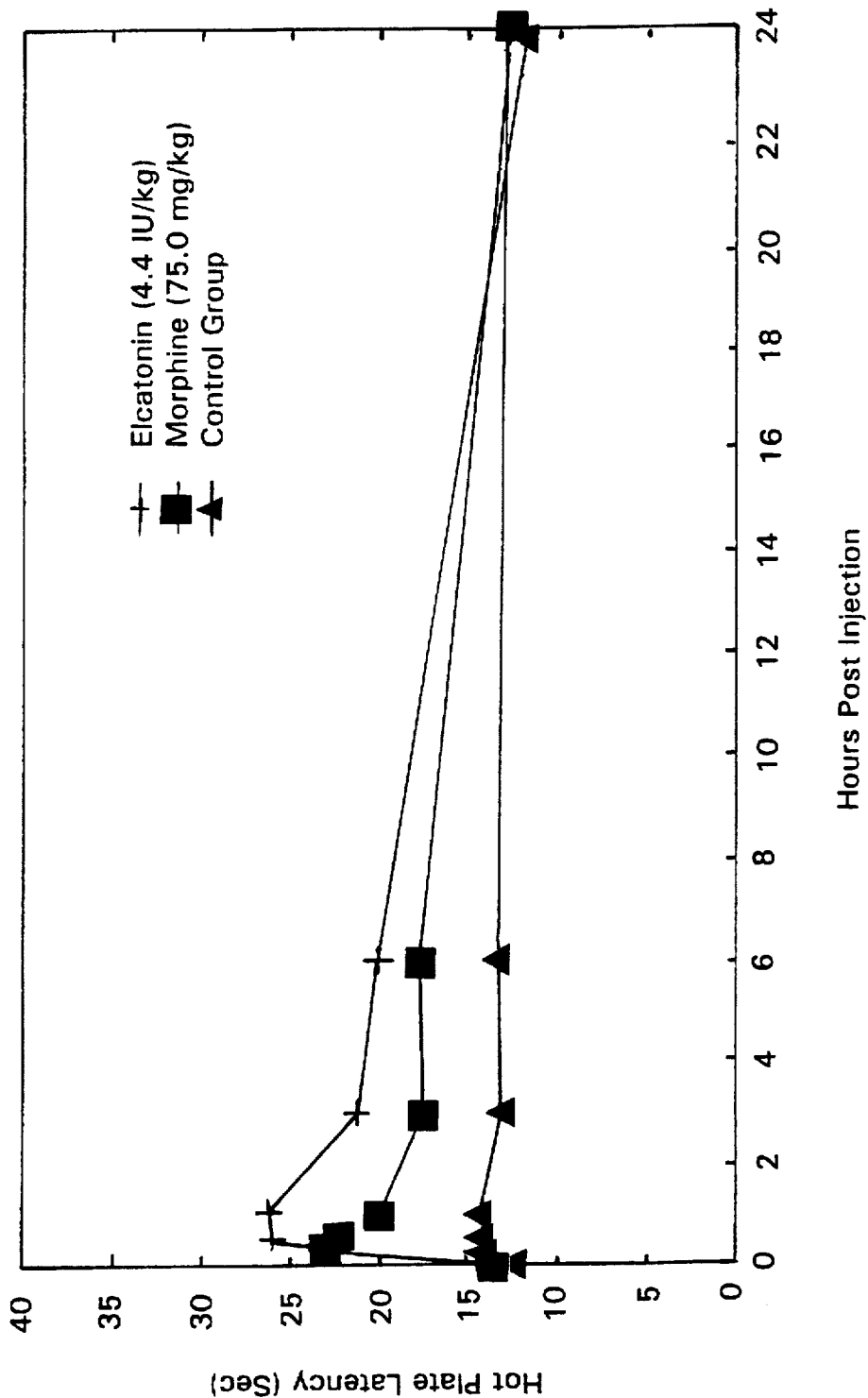
FIG. 5 provides a comparison of the time courses and increases in hot plate latency of intermediate doses of elcatonin (4.4 IU/kg, —▼—) and morphine (75.0 mg/kg, —■—). Physiological saline (—▲—) administered via the intrathecal route serves as a control. Maximum possible latency is 40 sec in these experiments.

All three doses of morphine increased hot plate latency in a dose-related fashion, and the onset of analgesia occurred within 15 min post-injection (Table 2, FIG. 3A). However, the duration of analgesia appeared to be shorter than for elcatonin, with reduced potency apparent by 3 hours post-injection, and a return toward baseline hot plate scores by 6 hours post-injection, particularly for the lower doses. In addition, the peak levels of analgesia achieved in morphine-injected animals were generally lower than that achieved elcatonin injected animals at the doses used in this study (Table 2, FIGS. 3A, 3B).

To compare analgesic potencies of elcatonin and morphine, doses were converted to nmol/kg. Dose-responsiveness to both drugs was plotted at several time points in order to estimate equivalent doses (Table 2). At 30 min post-injection, 0.12 nmol/kg elcatonin (2.4 IU/kg or 0.39 µg/kg) produced a not plate latency similar to 98.84 nmol/kg morphine sulfate (75.0 µg/kg), and 0.18 nmol/kg elcatonin (3.6 IU/kg or 0.58 µg/kg) is approximately equivalent to 164.73 nmol/kg morphine sulfate (125.0 µg/kg). Similar potencies are seen at 1 hour post-injection Table 2). However, at 6 hours post-injection, morphine antinociceptive activity was reduced compared to elcatonin, such that all tested doses of elcatonin (0.12–0.30 nmol/kg) resulted in more potent hot plate analgesia than all tested doses of morphine sulfate (49.42–164.73 nmol/kg) at this time point (Table 2).

Figure 6:
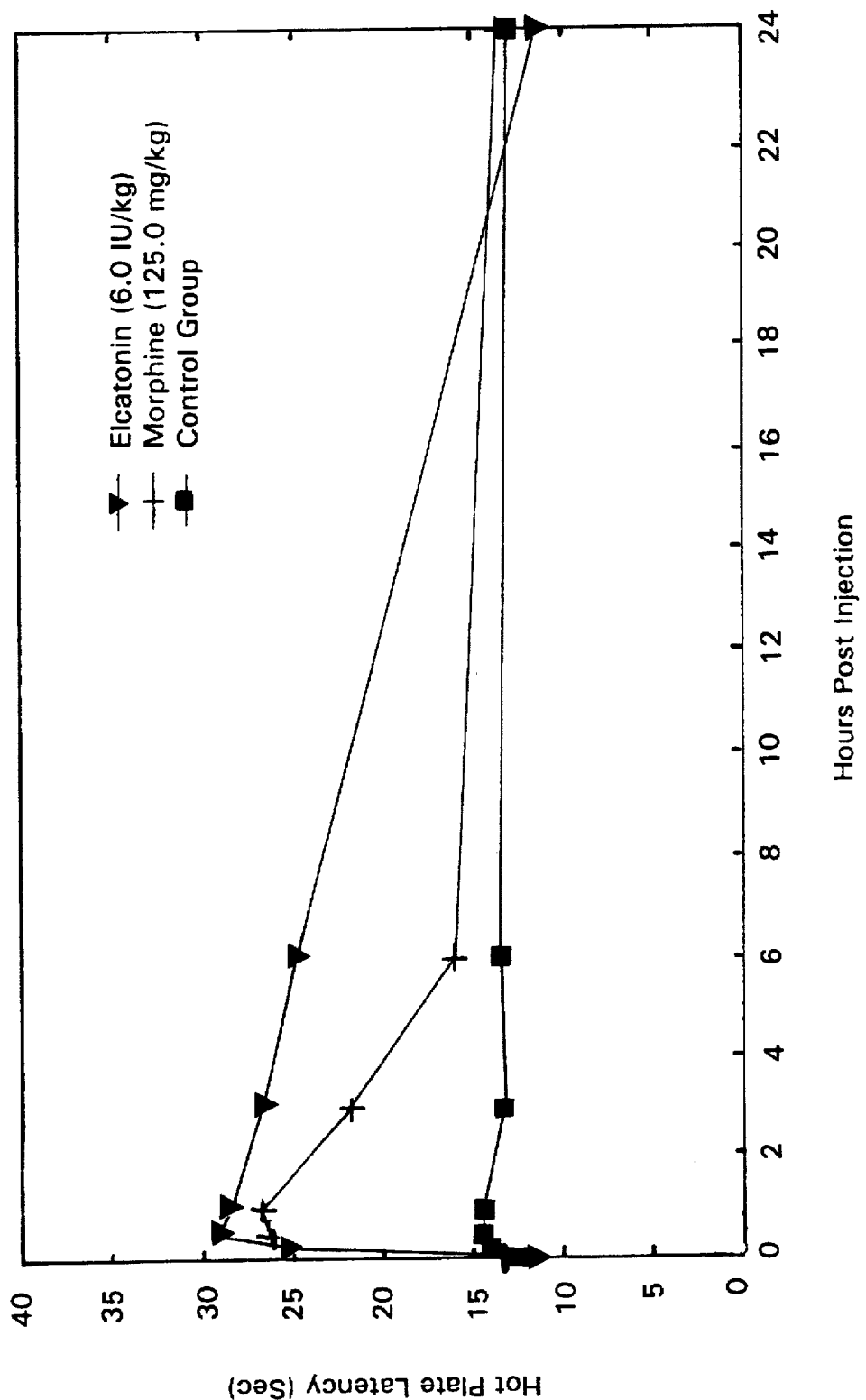
FIG. 6 provides a comparison of the time courses and increases in rat hot plate latency of high-dose for elcatonin (6.0 IU/kg, —▼—) and morphine (125 mg/kg, —●—). Physiological saline (—■—) administered via the intrathecal route serves as a control. Maximum possible latency is 40 sec.

To compare duration of analgesic activity, the time course of antinociception was compared for the lowest doses of elcatonin and morphine (FIG. 4), intermediate doses of elcatonin and morphine (FIG. 5), and highest doses of elcatonin and morphine (FIG. 6). It is apparent that elcatonin has a generally longer duration of analgesic activity than morphine, particularly apparent at low and intermediate doses. Vehicle injections did not produce detectable changes in hot plate latencies.

Body weight changes were unremarkable, and no mortality was observed. No clinical or behavioral abnormalities were noted within a 24 hour observation period following intrathecal administration of elcatonin. Short-Term tail (2) and hind limb (1) myoclonia occurred in two animals (3.6 and 5.2 IU/kg). In these experiments, no other significant morbidity or clinical and behavioral abnormalities were observed after the intrathecal administration of elcatonin.

TABLE 2

COMPARATIVE ANALGESIC ACTIVITY (HOT PLATE LATENCY) OF
ELCATONIN AND MORPHINE FOLLOWING SINGLE INTRATHECAL
ADMINISTRATION IN THE RAT (MEAN ± SEM)

| Group | No. of Rats | Dose IU/kg | µg/kg | nmol/kg | Hot Plate Latency (sec.) Time After Administration (hr.) | | | | | | |
|---|---|---|---|---|---|---|---|---|---|---|---|
| | | | | | 0 | 0.25 | 0.5 | 1 | 3 | 6 | 24 |
| Control (vehicle) | 15 | — | — | — | 12.51 ± 0.60 | 14.16 ± 0.64 | 14.32 ± 1.00 | 14.32 ± 1.02 | 13.16 ± 0.79 | 13.14 ± 0.74 | 12.85 ± 1.87 |
| Elcatonin | 9 | 2.4 | 0.39 | 0.12 | 13.54 ± 1.91 | 19.70 ± 1.75* | 23.90 ± 3.12 | 24.68 ± 1.80** | 13.0 ± 0.7* | 12.1 ± 0.5 | 10.8 ± 0.7 |
| | 10 | 3.6 | 0.58 | 0.18 | 12.92 ± 1.4 | 21.04 ± 2.22** | 26.03 ± 3.08** | 26.08 ± 3.69** | 23.14 ± 3.05** | 20.37 ± 3.44 | 15.79 ± 2.40 |
| | 9 | 4.4 | 0.71 | 0.22 | 13.68 ± 1.10 | 21.89 ± 3.12* | 26.03 ± 3.36** | 26.20 ± 2.37** | 21.11 ± 2.18* | 20.02 ± 3.26 | 11.78 ± 1.75 |
| | 8 | 5.2 | 0.84 | 0.26 | 13.41 ± 0.92 | 27.89 ± 3.10** | 31.55 ± 4.17** | 25.82 ± 3.79** | 28.81 ± 3.41** | 22.97 ± 2.60** | 12.36 ± 1.69 |
| | 9 | 6.0 | 0.97 | 0.30 | 11.38 ± 0.89 | 25.22 ± 4.13** | 28.91 ± 3.40** | 24.48 ± 3.35** | 26.60 ± 3.87** | 24.69 ± 2.84** | 11.17 ± 1.80 |
| Morphine | 9 | — | 37.5 | 49.42 | 12.81 ± 1.23 | 22.08 ± 2.68** | 20.97 ± 2.56** | 21.81 ± 2.46** | 19.97 ± 2.05* | 14.02 ± 1.24 | 11.33 ± 1.51 |
| | 9 | — | 75.0 | 98.84 | 13.76 ± 1.27 | 22.76 ± 2.43** | 21.86 ± 2.25** | 19.88 ± 2.04** | 17.42 ± 1.93 | 17.66 ± 1.71 | 12.60 ± 1.19 |
| | 9 | — | 125.0 | 164.73 | 13.28 ± 1.35 | 19.4 ± 1.6** | 26.36 ± 4.20** | 26.83 ± 3.04** | 21.69 ± 3.62* | 15.86 ± 3.29 | 13.49 ± 1.63 |

*p < 0.05 } compare to baseline
**p ≤ 0.01 (T-test)

In summary, these result indicate that elcatonin produces potent analgesia at approximately 1000-fold lower molar concentrations than morphine sulfate when administered via the intrathecal route and that the analgesia produced by elcatonin is sustained for prolonged periods, at least up to 6 hours post-injection, compared to morphine sulfate administered intrathecally.

Example 10: Analgesic Activity of Intravenous Elcatonin

This study sought to establish effective doses for analgesia of elcatonin administered by the intravenous route and to determine dose-responsiveness.

A total of 24 rats, ranging in weight from 320 to 420 g, was used in this study. Four to eight rats were used for each dose level. Elcatonin was administered in a volume of 0.5 ml/mg body weight by tail vein injection. The doses used were 10, 30, 100 and 300 IU/kg (1.61, 4.83, 16.1 and 48.3 µg/kg, respectively). Baseline hot plate responses and latencies at 15 min, 30 min, 1 hr, 3 hr, 6 hr and 24 hr after injection were determined in the hot plate analgesiometric assay described in Example 5 hereinabove.

The results in this study indicate that elcatonin injected intravenously produced only small increases in hot plate latencies, reflective of only small analgesic effects (Table 3).

TABLE 3

ANALGESIC ACTIVITY (HOT PLATE LATENCY) OF ELCATONIN
FOLLOWING SINGLE INTRAVENOUS ADMINISTRATION IN THE RAT)
(Mean ± SEM)

| Group | Dose IU/kg | µg/kg | No. of Rats | Hot Plate Latency (sec.) Time After Administration (hr.) | | | | | | |
|---|---|---|---|---|---|---|---|---|---|---|
| | | | | 0 | 0.25 | 0.5 | 1 | 3 | 6 | 24 |
| Elcatonin in | 10.0 | 1.61 | 8 | 12.03 ± 1.02 | 11.95 ± 1.40 | 15.64 ± 2.39 | 14.95 ± 2.92 | 14.11 ± 0.94 | 10.45 ± 1.03 | 8.86 ± 1.23 |
| | 30.0 | 4.83 | 8 | 10.71 ± 1.02 | 10.04 ± 0.96 | 12.18 ± 1.22 | 14.14 ± 1.14 | 14.26 ± 1.39 | 15.12 ± 2.20 | 10.76 ± 1.25 |
| | 100.0 | 16.1 | 4 | 13.53 ± 1.63 | 11.05 ± 1.99 | 9.63 ± 1.21 | 11.20 ± 1.95 | 14.76 ± 1.19 | 14.00 ± 1.83 | 14.30 ± 1.33 |
| | 300.0 | 48.3 | 4 | 11.22 ± 0.38 | 11.05 ± 3.82 | 11.65 ± 2.31 | 12.65 ± 2.09 | 17.37 ± 4.25 | 11.55 ± 2.80 | 10.52 ± 1.74 |

No increases in apparent analgesic effects were observed for the higher doses (100 and 300 IU/kg) as compared with the lower dose ranges (10 and 30 IU/kg) although the peak effects appeared to occur late (at 3–6 hr) and slightly prolonged for the 30–300 IU/kg doses as compared to 30 min for the 10 IU/kg dose. No significant dose response effect was observed for elcatonin administered by the intravenous route at doses from 10 to 300 IU/kg body weight in the rat (Table 3).

A comparative analysis of the hot plate latencies obtained after intravenous and intrathecal administration of elcatonin indicates that at 0.5 hr the lowest intravenous dose of elcatonin (10.0 IU/kg or 1.61 µg/kg) produces a hot plate latency similar to that produced by 1.6 IU/kg (0.25 µg/kg) of elcatonin administered via intrathecal route (See Example 8).

In these experiments, no significant body weight changes, morbidity, mortality or clinical and behavioral abnormalities were observed after the intravenous injection of elcatonin.

Example 11: Analgesic Activity of Multiple Intrathecal Doses of Elcatonin

This study assesses the effectiveness of repeated doses of intrathecally administered elcatonin for analgesia. Intrathecal catheters were implanted in rats as described hereinabove, and a 7–10 day period thereafter allowed for full recovery from the surgical procedures.

Eighteen rats were assigned to three treatment groups of six rats per group. The study is conducted in two treatment phases at one week intervals. Treatment Group I rats receive no treatment. Group II rats receive five consecutive daily intrathecal doses of sterile physiological saline (vehicle control). Group III rats receive five consecutive daily doses of elcatonin (4.4 IU/kg body weight).

For each treatment, hot plate latencies are determined as described in Example 5 herein above at 0 minutes (predose, baseline), 1 hour, 3 hours, and 24 hours following injection on the first, third, and fifth study days.

Figure 7:
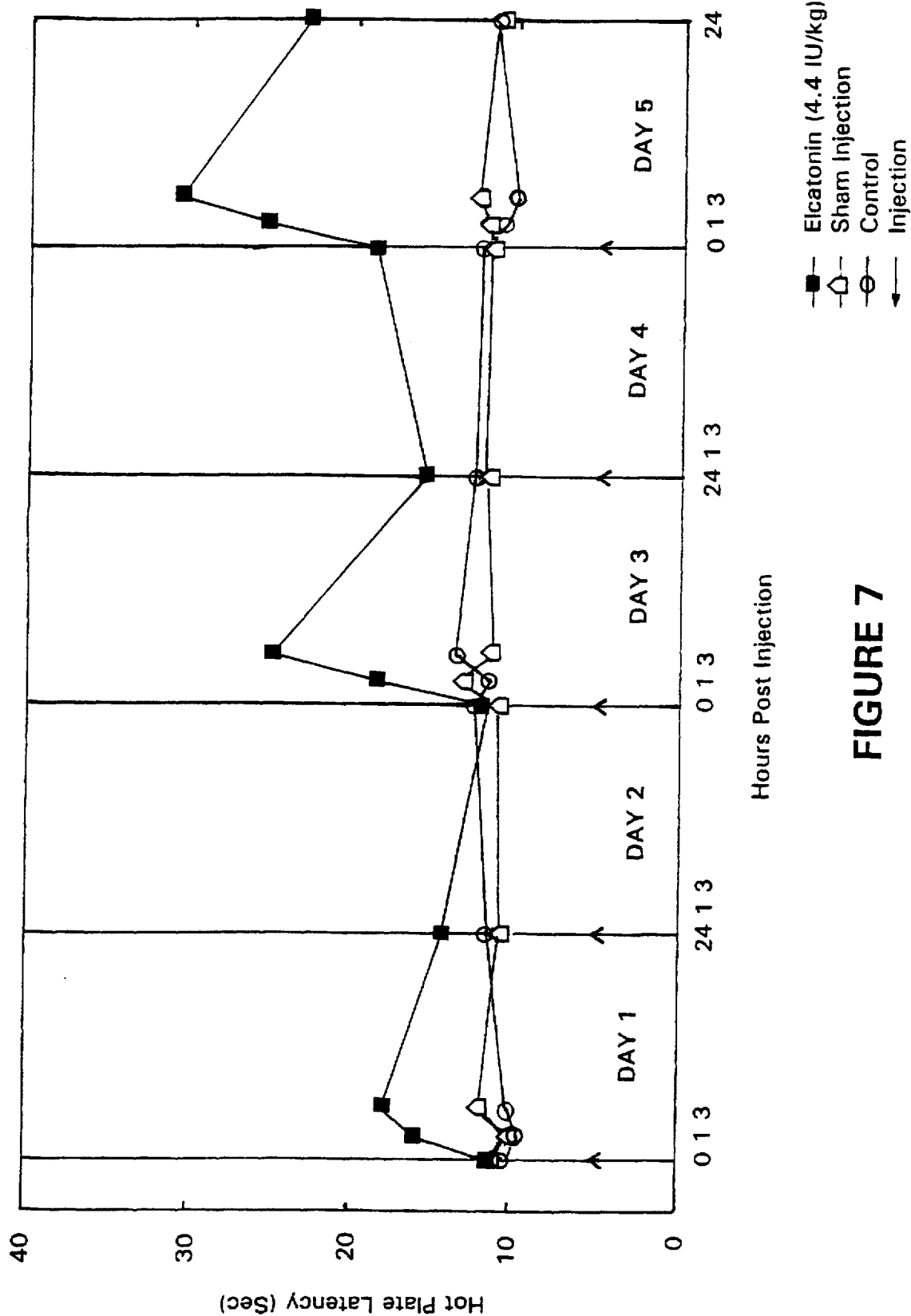
FIG. 7 illustrates the increase in rat hot plate latency after 5 days multiple intrathecal administrations of elcatonin at a dose of 4.4 IU/kg body weight (—■—) as compared with physiological saline (—○—) or sham injection (—♦—). The vertical arrows indicate the times when rats were injected. Hot plate latency was measured at 0, 1, 3 and 24 hrs after injection on study days 1, 3 and 5.

The results in FIG. 7 show that hot plate latency is increased by repeated intrathecal doses of elcatonin, and it appears that at 24 hr after each successive injection, there is greater hot plate latency, and a cumulative analgesic effect over time.

In these experiments, no significant body weight changes, morbidity, mortality or clinical and behavioral abnormalities were observed after the intrathecal administration of elcatonin.

Example 12: Analgesic Activity of 10 Single Daily Intrathecal Doses of Elcatonin Over 11 Days in the Rat This study assesses the effectiveness of repeated doses of 10 single consecutive daily doses of elcatonin administered via the intrathecal route in the rat during two 5 day treatment phases separated by a 48 hour nontreatment interval.

Intrathecal catheters were implanted in rats as described hereinabove, and a 7–10 day period thereafter allowed for full recovery from the surgical procedures. Nine rats were assigned to three treatment groups of three rats per group. The study is conducted in two 5 day treatment phases separated by a 48 hour nontreatment interval. Treatment Group I rats receive no treatment (sham injection). In each treatment phase, Group II rats received five consecutive daily intrathecal doses of sterile physiological saline (vehicle control), for a total of 10 injections per study treatment. In each treatment phase, Group III rats each received five consecutive daily doses of elcatonin (4.4 IU/kg body weight), for a total of 10 injections per study treatment (Table 4).

For each treatment, hot plate latencies are determined as described in Example 5 hereinabove at 0 minutes (predose, baseline), 1 hour, 3 hours, and 24 hours following injection on the 1st, 3rd, 5th, 7th, 9th and 11th study days (Table 4).

Figure 8:
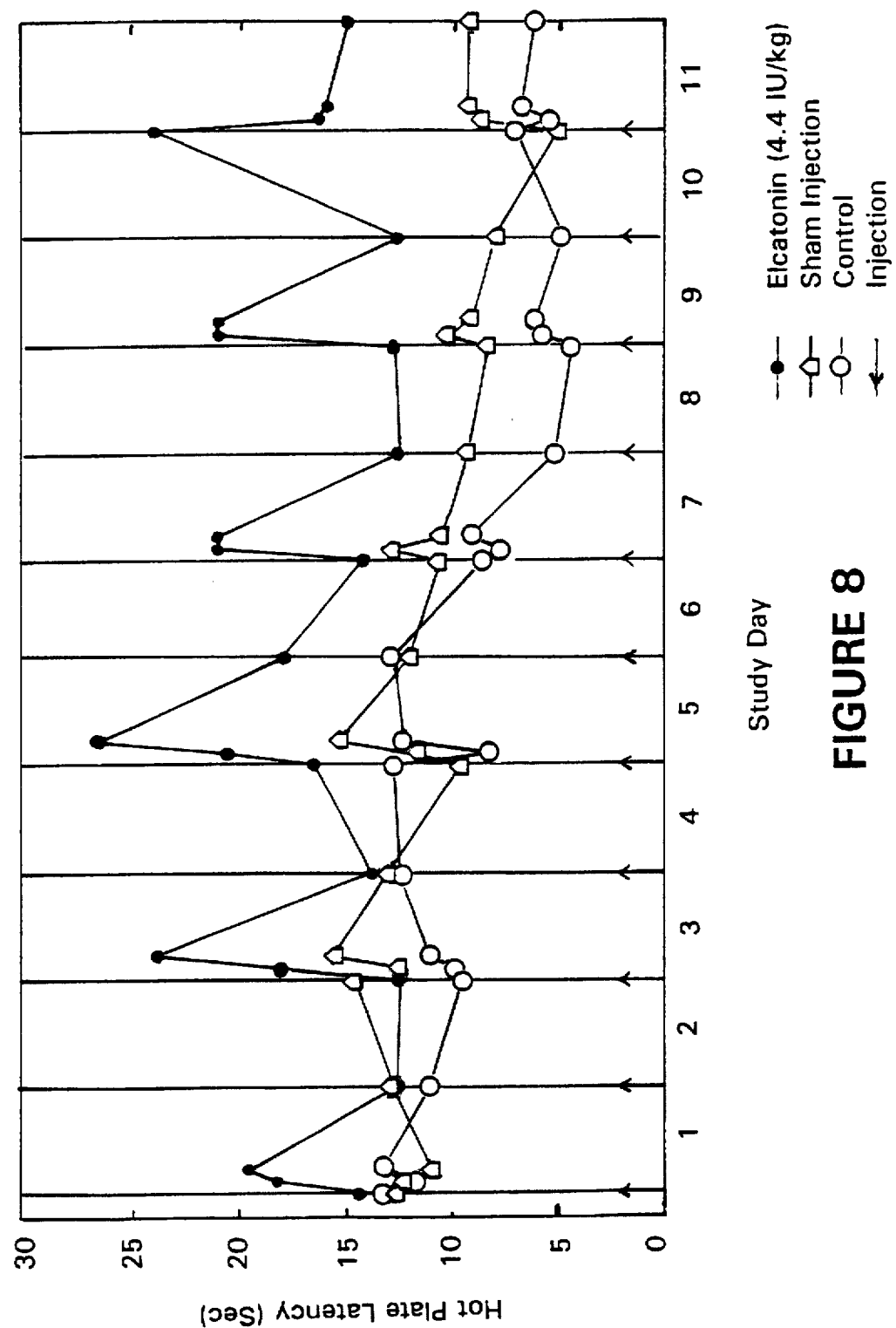
FIG. 8 illustrates the increase in rat hot plate latency after 10 single daily intrathecal injections of elcatonin at a dose of 4.4 U/kg (—■—) as compared to latency for saline vehicle (—○—) or sham injection (—Δ—), separated by 48 hrs non-treatment intervals. The vertical arrows indicate the times when rats were injected. Hot plate latency was measured at 0, 1, 3 and 24 hrs after injection on study days 13, 5, 7, 9 and 11.

The results in FIG. 8 show that hot plate latency is increased by repeated intrathecal doses of elcatonin, and there is a cumulative analgesic effect over time.

In these experiments, no significant body weight changes, morbidity, mortality or clinical and behavioral abnormalities were observed after the intrathecal administration of elcatonin.

TABLE 4

| | STUDY DESIGN | | | | | | | | | | | |
|---|---|---|---|---|---|---|---|---|---|---|---|---|
| | Study Day | | | | | | | | | | | |
| Procedure | 1 | 2 | 3 | 4 | 5 | 6 | 7 | 8 | 9 | 10 | 11 | 12 |
| Phase 1 | | | | | | | | | | | | |
| Injection | x | x | x | x | x | | | | | | | |
| Hot plate test | x | | x | | x | | | | | | | |
| Metabolic observation | x | x | x | x | x | x | | | | | | |
| Clinical observation | x | x | x | x | x | x | | | | | | |
| Phase 2 | | | | | | | | | | | | |
| Injection | | | | | | | x | x | x | x | x | |
| Hot plate test | | | | | | | x | | x | | x | |
| Metabolic observation | | | | | | | x | x | x | x | x | x |
| Clinical observation | | | | | | | x | x | x | x | x | x |

Example 13: Human Serum Albumin-Containing Pharmaceutical Compositions

This study is conducted to evaluate the effect of human serum albumin as an ingredient in elcatonin-containing analgesic composition. Human serum albumin (HSA) is a candidate to prevent adherence of elcatonin to the vials or tubing (or the like) before administration to a patient or experimental animal.

On each study day, a standard 25% (wt/vol) solution of HSA is diluted under aseptic conditions with physiological saline (0.3% solution of NaCl, USP grade) to achieve the desired stock solution concentration of 0.2% (wt/vol). Where needed, an aliquot of elcatonin solution was mixed with an equal volume of 0.2% HSA to give a final concentration of 0.1% HSA in the elcatonin-containing composition for administration.

Thirty-two male rats (320–420 g) are obtained, adapted, catheterized and recovered as described hereinabove. Group I rats are injected intrathecally with elcatonin in physiological saline at a dose of 4.4 IU/kg, in a volume of 10 μl/kg. Group II rats are injected intrathecally with a dose of 4.4 IU/kg in physiological saline containing 0.1% HSA, in a volume of 10 μL/kg. Group III rats are injected with physiological saline containing 0.1% HSA, 10 μL/kg. Each dose is followed by a washout of 8 μL of physiological saline.

Figure 9:
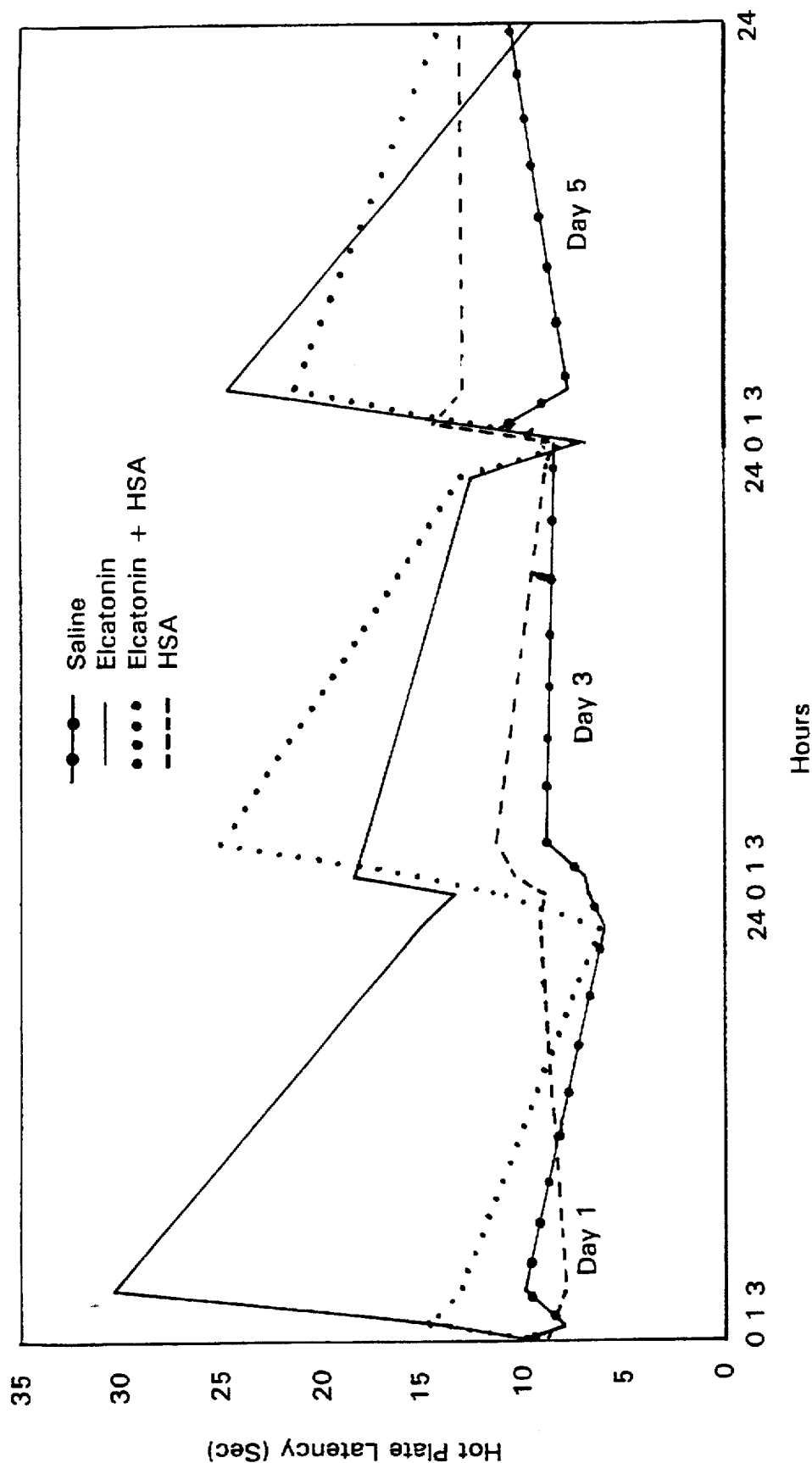
FIG. 9 illustrates the increase in rat hot plate latency after 5 days multiple intrathecal administration of elcatonin (at a dose of 4.4 IU/kg) with HSA (0.1%). Hot plate latency was measured at 0, 1, 3 and 24 hrs after injection on study days 1, 3 and 5.

In each of the study groups, hot plate latencies are determined at 0 minutes (baseline, predose), 1 hour, 3 hours, 6 hours, and 24 hours following intrathecal injections on the 1st, 3rd and 5th study days. The results in FIG. 9 show increase in rat hot plate latency after 5 day multiple intrathecal administrations of elcatonin (at a dose of 4.4 IU/kg, in 0.1% HSA).

In these experiments, no significant body weight changes, morbidity, mortality or clinical and behavioral abnormalities were observed after the intrathecal of elcatonin.

Example 14: Pharmacokinetics of $^{125}$I-Elcatonin in the Rat Following Intravenous and Intrathecal Administration Pharmacokinetics/mass balance and tissue distribution in selected tissues were studied in 21 male Sprague-Dawley rats according to the study design described in Table 5.

Radioiodinated elcatonin ($^{125}$I-Elcatonin) was administered intravenously (IV) via the jugular vein and intrathecally (IT) via a surgically implanted catheter. Blood, plasma, urine, feces, tissue and carcass samples were collected at specified times (Table 5) following a single 1 µg/kg IT bolus dose or a single 50 µg/kg IV bolus dose.

TABLE 5

STUDY DESIGN AND SCHEDULE OF SAMPLE COLLECTION

| Animal Group (n) | Dosing Route | Dose(s) | Biological Samples for Total Radioactivity Measurement | Sampling Times |
|---|---|---|---|---|
| 1 (n = 4) | IV (Bolus) | Single dose: 50 µg/kg of $^{125}$I-Elcatonin (20 µci/µg) Injection volume: 1 mL/kg | 8 plasma samples per animal Brain, spinal cord, lung, liver, thyroid, kidney, blood and plasma samples from 2 animals. (A total of 34 plasma, 2 blood, and 12 tissue samples) | Blood: 5 min, 0.5, 1, 2, 4, 8, 24 and 48 hr post-dose Tissues, blood and plasma: 120 hr post-dose (n = 2 rats) |
| 2 (n = 4) | Intrathecal | Single dose: 1 µg/kg of $^{125}$I-Elcatonin (20 µci/µg) Injection volume: 20 µL/kg | 8 plasma samples per animal Brain, spinal cord, lung, liver, thyroid, kidney, blood and plasma samples from 2 animals. (A total of 34 plasma, 2 blood, and 12 tissue samples) | Blood: 0.5, 1, 2, 4, 6, 8, 24 and 48 hr post-dose Tissues, blood and plasma: 120 hr post-dose (n = 2 rats) |
| 3 (n = 4) | IV (Bolus) | Single dose: 50 µg/kg of $^{125}$I-Elcatonin (20 µci/µg) Injection volume: 1 mL/kg | 7 urine and 5 fecal samples per animal 1 Carcass sample per animal (A total of 4 carcass, 28 urine and 20 fecal samples). Cage washes | Urine: 0-6, 6-12, 12-24, 24-48, 48-72, 72-96 and 96-120 hr post-dose Feces: 0-24, 24-48, 48-72, 72-96 and 96-120 hr post-dose Carcass: 120 hr post-dose |
| 4 (n = 4) | IV (Bolus) | Single dose: 50 µg/kg of $^{125}$I-Elcatonin (20 µci/µg) Injection Volume: 1 mL/kg | Brain, spinal cord, lung, liver, thyroid, kidney, blood and plasma samples per each animal. (A total of 24 tissue, 4 blood and 4 plasma samples). | Tissues, blood and plasma: 1 hr post-dose (n = 2 rats) and 24 hr post-dose (n = 2 rats) |
| 5 (n = 4) | Intrathecal | Single dose: 1 µg/kg of $^{125}$I-Elcatonin (20 µci/µg) Injection Volume: 20 µL/kg | Brain, spinal cord, lung, liver, thyroid kidney, blood and plasma samples per each animal. (A total of 24 tissue, 4 blood and 4 plasma samples). | Tissues, blood and plasma: 1 hr post-dose (n = 2 rats) and 24 hr post-dose (n = 2 rats) |
| 6 (n = 1) | non-dosed | No dose | Urine, feces, blood plasma, tissues, carcass and cage washes | Samples were collected at 24 hours for analysis of background |

Total radioactivity was measured using a Gamma Counter. In addition, protein-associated radioactivity in plasma was estimated by measuring radioactivity in the plasma proteins afterprecipitation with trichloroacetic acid.

The terminal phase half-life of total radioactivity (free $I_2$ and iodinated proteins) in plasma was 29 hrs following intravenous dosing and 32 hrs following intrathecal dosing. The terminal phase half-lives for TCA-precipitable radioactivity following intravenous and intrathecal dosing were similar (estimated to be 40 hrs). Following intrathecal dosing, drug-derived radioactivity distributed relatively rapidly to tissues ($C_{max}$ at 1 h). The rank order of concentration for tissues analyzed was thyroid>spinal cord>brain>kidney>blood>lungs>liver. Without wishing to be bound by any particular theory, the high concentration of radioactivity in the thyroid is most likely a consequence of the presence of free $I_2$ in the dosing preparation. The brain plasma radioactivity levels were significantly higher after intrathecal administration than after intravenous dosing, indicating poor crossing of the blood/brain barrier. Eighty-six percent of the dose was recovered following IV dosing. Approximately 46% of the administered radioactivity was recovered in the first 24 hrs. The major route of elimination was via the urine (71% dose).

We claim:

1. A method for treating intractable pain in a human, said method comprising the step of administering via an intrathecal route a composition comprising a therapeutically effective amount of elcatonin and a pharmaceutically acceptable vehicle.

2. The method of claim 1 wherein said elcatonin is a non-narcotic analgesic with a central mechanism of action independent from opiate receptors.

3. The method of claim 1 wherein said elcatonin is administered in a dose of from about 0.2 IU to about 15 IU per kg body weight.

4. The method of claim 3 wherein said elcatonin is administered in a dose of from about 1.6 to about 6.4 IU/kg body weight.

5. The method of claim 1 wherein said composition is administered in a volume of from about 0.7 to 2.0 ml.

6. The method of claim 1 wherein said pharmaceutically acceptable vehicle is sterile isotonic saline.

7. The method of claim 1 wherein said intractable pain is associated with cancer.

8. The method of claim 1 wherein said composition is administered via the intrathecal route as a single injection or by multiple bolus injection.

9. The method of claim 1 wherein said composition is administered via the intrathecal route at intervals between doses up to 48 hours.

10. The method of claim 1 wherein said composition is administered via the intrathecal route by continuous infusion.

11. The method of claim 1 wherein said composition further comprises human serum albumin.

12. The method of claim 11 wherein said human serum albumin is present at a concentration of about 0.1%.

13. The method of claim 1 wherein said composition is administered in a standard volume for intrathecal or epidural administration.

* * * * *

UNITED STATES PATENT AND TRADEMARK OFFICE
CERTIFICATE OF CORRECTION

PATENT NO. : 5,721,207

DATED : February 24, 1998

INVENTOR(S) : John F. Noble and Henry B. Abajian

It is certified that error appears in the above-identified patent and that said Letters Patent is hereby corrected as shown below:

On the title page, column 2, under *Assistant Examiner*, delete "Pihynn Tozeam" and replace with --P. Lynn Touzeau--.

Column 2, line 10, please delete "¤" and replace with --□--.

Column 2, line 40, please delete "♦" and replace with --◊--.

Column 2, line 48, please delete "△" and replace with --◊--.

Column 2, line 51, please delete "13," and replace with --1, 3,--.

Column 5, line 10, please delete "Spraque-Dawley" and replace with --Sprague-Dawley--.

Column 5, line 11, please delete "Spraque-Dawley" and replace with --Sprague-Dawley--.

Column 5, line 18, please delete "of group" and replace with --of the group--.

Column 6, line 55, please delete "ume 0.5" and replace with --ume of 0.5--.

Column 7, line 46, please delete "with a dose" and replace with --with dose--.

Column 8, line 19, please delete "achieved" and replace with --achieved by--.

Column 8, line 28, please delete "not plate" and replace with --hot plate--.

Column 8, line 32, please delete "post-injection Table 2)." and replace with --post-injection (Table 2).--.

UNITED STATES PATENT AND TRADEMARK OFFICE
CERTIFICATE OF CORRECTION

PATENT NO. : 5,721,207

DATED : February 24, 1998

INVENTOR(S) : John F. Noble and Henry B. Abajian

It is certified that error appears in the above-identified patent and that said Letters Patent is hereby corrected as shown below:

Column 10, in Table 2, under the heading of Hot Plate Latency, the column numbered 1, the 6$^{th}$ row down, delete "24.48" and replace with --28.48--.

Column 10, in Table 2, under the heading of Hot Plate Latency, the column numbered 1, the 8$^{th}$ row down, delete "2.04**" and replace with --2.04*--.

Column 9, line 29, delete "result" and replace with --results--.

Column 12, line 60, delete "intrathecal of" and replace with --intrathecal administration of--.

Column 13, line 49, delete "afterprecipitation" and replace with --after precipitation--.

Signed and Sealed this

Twelfth Day of May, 1998

BRUCE LEHMAN

*Attest:*

*Attesting Officer*            *Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Eel ( x i ) SEQUENCE DESCRIPTION: SEQ ID NO:1:

```
Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
            20                  25                  30
```

( 2 ) INFORMATION FOR SEQ ID NO:2:

( i ) SEQUENCE CHARACTERISTICS:
        ( A ) LENGTH: 33 amino acids
        ( B ) TYPE: amino acid
        ( C ) STRANDEDNESS:
        ( D ) TOPOLOGY: linear ( i i ) MOLECULE TYPE: peptide ( v i ) ORIGINAL SOURCE:
        ( A ) ORGANISM: Homo sapiens ( x i ) SEQUENCE DESCRIPTION: SEQ ID NO:2:

```
Cys Gly Asn Leu Ser Thr Cys Val Met Leu Gly Thr Tyr Thr Gln Asp
1               5                   10                  15

Phe Asn Lys Phe His Thr Phe Pro Gln Thr Ala Ile Gly Val Gly Ala
            20                  25                  30

Pro
```

( 2 ) INFORMATION FOR SEQ ID NO:3:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Porcine ( x i ) SEQUENCE DESCRIPTION: SEQ ID NO:3:

```
Cys Ser Asn Leu Ser Thr Cys Val Leu Ser Ala Tyr Trp Arg Asn Leu
1               5                   10                  15

Asn Asn Phe His Arg Phe Ser Gly Met Gly Phe Gly Pro Glu Thr Pro
            20                  25                  30
```

( 2 ) INFORMATION FOR SEQ ID NO:4:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Salmon ( x i ) SEQUENCE DESCRIPTION: SEQ ID NO:4:

```
Cys Ser Asn Leu Ser Thr Cys Val Leu Gly Lys Leu Ser Gln Glu Leu
 1               5                  10                  15

His Lys Leu Gln Thr Tyr Pro Arg Thr Asn Thr Gly Ser Gly Thr Pro
             20                  25                  30
```

( 2 ) INFORMATION FOR SEQ ID NO:5:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Rat ( x i ) SEQUENCE DESCRIPTION: SEQ ID NO:5:

```
Cys Gly Asn Leu Ser Thr Cys Met Leu Gly Thr Tyr Thr Gln Asp Leu
 1               5                  10                  15

Asn Lys Phe His Thr Phe Pro Gln Thr Ser Ile Gly Val Gly Ala Pro
             20                  25                  30
```